United States Patent
Tanaka et al.

(10) Patent No.: US 12,351,369 B2
(45) Date of Patent: Jul. 8, 2025

(54) INNER PLUG CONSTITUTING NOZZLE AND EYE DROP CONTAINER

(71) Applicant: Fujimori Kogyo Co., Ltd., Tokyo (JP)

(72) Inventors: Yoshitoh Tanaka, Yokohama (JP); Asako Kanazawa, Yokohama (JP); Toyoaki Suzuki, Yokohama (JP)

(73) Assignee: ZACROS Corporation, Tokyo (JP)

( * ) Notice: Subject to any disclaimer, the term of this patent is extended or adjusted under 35 U.S.C. 154(b) by 205 days.

(21) Appl. No.: 17/793,731

(22) PCT Filed: Jan. 20, 2021

(86) PCT No.: PCT/JP2021/001816
§ 371 (c)(1),
(2) Date: Jul. 19, 2022

(87) PCT Pub. No.: WO2021/149712
PCT Pub. Date: Jul. 29, 2021

(65) Prior Publication Data
US 2023/0088243 A1    Mar. 23, 2023

(30) Foreign Application Priority Data
Jan. 21, 2020    (JP) ................. 2020-007831

(51) Int. Cl.
*B65D 47/18*    (2006.01)
*A61F 9/00*    (2006.01)
(Continued)

(52) U.S. Cl.
CPC ............ *B65D 47/18* (2013.01); *A61F 9/0008* (2013.01); *A61J 1/05* (2013.01); *B65D 53/02* (2013.01)

(58) Field of Classification Search
CPC ........ B65D 47/18; B65D 53/02; A61F 9/0008; A61J 1/05; A61J 1/1412; A61J 1/1468
See application file for complete search history.

(56) References Cited

U.S. PATENT DOCUMENTS 1,147,384 A * 7/1915 Fetzer, Jr. ............ B65D 47/122
222/562
1,436,708 A * 11/1922 Goebel .................. B65D 47/06
215/309
(Continued)

FOREIGN PATENT DOCUMENTS

| CN | 101754742 A | 6/2010 |
|---|---|---|
| CN | 102574615 A | 7/2012 |

(Continued)

OTHER PUBLICATIONS

Search Report from Chinese Patent Office for Application No. 202180010049.3 dated Jan. 22, 2024 (translation included).
(Continued)

*Primary Examiner* — Bob Zadeh
(74) *Attorney, Agent, or Firm* — Harris Beach Murtha Cullina PLLC

(57) ABSTRACT

The eye drop container includes a container body having an inner plug and an opening part in which the inner plug is mounted. The inner plug is mounted in the opening part of the container body, constitutes a nozzle part, and has a liquid-contacting part which is constituted of a layer including a cyclic olefin copolymer, a cushioning part which is provided in an outer circumferential part in contact with the opening part, a flange part which comes into contact with a tip surface of the opening part, and a leg part which comes into contact with an inner surface of the opening part. The cushioning part is provided on at least an outer circumferential surface of the leg part.

11 Claims, 2 Drawing Sheets

(51) Int. Cl.
*A61J 1/05* (2006.01)
*B65D 53/02* (2006.01)

(56) References Cited

U.S. PATENT DOCUMENTS

| | | | | |
|---|---|---|---|---|
| 1,478,035 | A * | 12/1923 | Hothersall | B65D 47/18 222/542 |
| 2,727,659 | A * | 12/1955 | Nyden | F16N 3/04 29/520 |
| 3,422,998 | A * | 1/1969 | Murray | B65D 51/10 D9/450 |
| 8,444,610 | B2 * | 5/2013 | Grevin | B65D 50/046 604/298 |
| 2005/0031812 | A1 | 2/2005 | Suzuki | |
| 2005/0043693 | A1 * | 2/2005 | Infantolino | A61M 35/003 604/300 |
| 2005/0139611 | A1 * | 6/2005 | Kubo | B65D 51/1616 222/189.06 |
| 2006/0165928 | A1 | 7/2006 | Suzuki et al. | |
| 2008/0021381 | A1 * | 1/2008 | Lurvey | A61M 39/16 604/87 |
| 2008/0141454 | A1 * | 6/2008 | Blomet | A61H 35/02 4/620 |
| 2009/0008416 | A1 * | 1/2009 | Kurosawa | B65D 75/5883 425/577 |
| 2009/0179052 | A1 * | 7/2009 | Allen | B65D 47/06 222/479 |
| 2011/0266184 | A1 * | 11/2011 | Suzuki | B32B 27/08 206/524.1 |
| 2011/0297703 | A1 * | 12/2011 | Wilson | B65D 47/18 222/571 |
| 2016/0151550 | A1 * | 6/2016 | Fisher | A61M 1/63 210/418 |
| 2017/0144783 | A1 * | 5/2017 | Komatsu | B65D 1/02 |
| 2018/0042766 | A1 * | 2/2018 | Nagao | A61F 9/0008 |
| 2019/0125877 | A1 | 5/2019 | Matsumura | |
| 2020/0122898 | A1 | 4/2020 | Ikeda et al. | |

FOREIGN PATENT DOCUMENTS

| | | | | |
|---|---|---|---|---|
| CN | 105324169 | A | 2/2016 | |
| CN | 105593138 | A | 5/2016 | |
| CN | 107108066 | A | 8/2017 | |
| CN | 107614391 | A | 1/2018 | |
| FR | 2915971 | A1 * | 11/2008 | G01F 11/262 |
| JP | 48-29316 | Y1 | 9/1973 | |
| JP | 2015535782 | A | 12/2005 | |
| JP | 2015016871 | A | 1/2015 | |
| JP | 2015107322 | A | 6/2015 | |
| JP | 2017145039 | A | 8/2017 | |
| JP | 2017197524 | A | 11/2017 | |
| WO | 03043895 | A1 | 5/2003 | |
| WO | 2004080370 | A1 | 9/2004 | |
| WO | 2018190422 | A1 | 10/2018 | |

OTHER PUBLICATIONS

International Search Report from corresponding Application No. PCT/JP2021/001816 dated Mar. 30, 2021.

\* cited by examiner

INNER PLUG CONSTITUTING NOZZLE AND EYE DROP CONTAINER

FIELD OF THE INVENTION

The present invention relates to an inner plug constituting a nozzle and an eye drop container including the same.

CROSS-REFERENCE TO RELATED APPLICATIONS

Priority is claimed on Japanese Patent Application No. 2020-007831, filed Jan. 21, 2020, the content of which is incorporated herein by reference.

BACKGROUND OF THE INVENTION

In the related art, regarding eye drop containers for storing eye drops, resin containers made of polyethylene (PE), polypropylene (PP), polyethylene terephthalate (PET), or the like are widely used. Patent Literature 1 (Japanese Unexamined Patent Application, First Publication No. 2015-107322) describes that an eye drop container including a container body constituted of a resin molded article is seal-packaged with a predetermined laminated film. The container body includes a storage part for eye drops and a nozzle part protruding from the storage part and is constituted such that eye drops can be applied from the eye drop container by pressurizing the storage part with the fingers while pointing the nozzle part toward the eye.

Regarding a resin for constituting an eye drop container in the related art, polyethylene or the like is inexpensive but has a disadvantage that chemical agents (active components or the like) are likely to be adsorbed thereby. Regarding a packaging container such as a packaging bag, a cyclic olefin copolymer is known as a resin having excellent non-adsorption properties with respect to content components—see, e.g., Patent Literature 2 (PCT International Publication No. WO 2003/043895) and Patent Literature 3 (PCT International Publication No. WO 2004/080370).

SUMMARY OF THE INVENTION

Technical Problem

In order to suppress sorption (adsorption or absorption) of eye drops in a storage part, there is a need to employ a material which is unlikely to sorb active components of eye drops. However, according to the investigation of the inventors, when a cyclic olefin copolymer is used in an inner plug, since the cyclic olefin copolymer is harder than resins such as PE, PP, and PET described above, it has been ascertained that a gap is generated between the inner plug and a container body resulting in problems of leakage or inflow of water vapor, a chemical agent, or the like through this gap.

The present invention has been made in consideration of the foregoing circumstances and aims to provide an inner plug, in which a gap is unlikely to be generated between a container body and the inner plug while sorption (adsorption, absorption) of eye drops is suppressed, and an eye drop container including the same.

Solution to Problem

In order to resolve the foregoing problems, according to an aspect of the present invention, there is provided an inner plug mounted in an opening part of a container body and constituting a nozzle. The inner plug includes a liquid-contacting part that is constituted of a layer including a cyclic olefin copolymer, and a cushioning part that is provided in an outer circumferential part in contact with the opening part.

The inner plug may have a flange part which comes into contact with a tip surface of the opening part, and a leg part which comes into contact with an inner surface of the opening part. The cushioning part may be provided on at least an outer circumferential surface of the leg part.

The outer circumferential part in contact with the opening part of the inner plug may have a part in which the liquid-contacting part directly comes into contact with the inner surface of the opening part on a side closer to a storage part of the container body than a part in contact with the inner surface of the opening part via the cushioning part.

The cushioning part may be constituted of a material of one or more kinds selected from a polyethylene resin, a rubber, and an elastomer.

The layer including the cyclic olefin copolymer may include at least one kind of a copolymer of cyclic olefins different from each other (COP) and a copolymer of a cyclic olefin and an acyclic olefin (COC).

According to another aspect of the present invention, there is provided an eye drop container including the inner plug, and a container body that has an opening part in which the inner plug is mounted.

The container body may have a layer including a cyclic olefin copolymer on at least a surface in contact with a liquid content.

Advantageous Effects of Invention

The inner plug according to the aspect of the present invention has a liquid-contacting part that is constituted of a layer including a cyclic olefin copolymer having excellent non-sorption properties, and a cushioning part that is provided in an outer circumferential part in contact with an opening part. Therefore, generation of a gap between a container body and the inner plug can be suppressed while sorption (adsorption, absorption) of eye drops is suppressed.

In addition, according to the eye drop container of another aspect, generation of a gap between a container body and the inner plug can be suppressed while sorption (adsorption, absorption) of eye drops is suppressed.

DETAILED DESCRIPTION OF THE INVENTION

Hereinafter, the present invention will be described with reference to the drawings on the basis of preferred embodiments.

Figure 1:
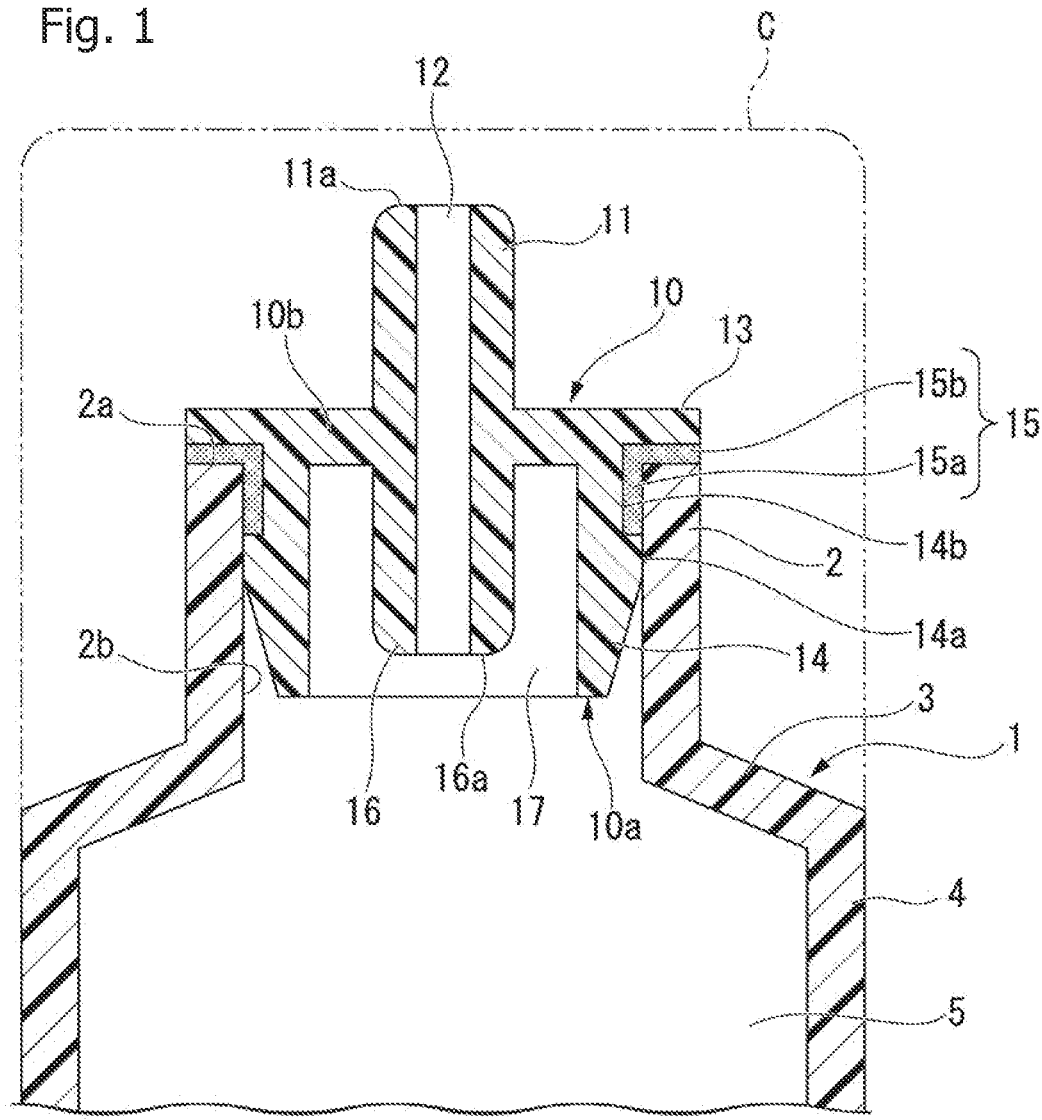
FIG. 1 is a cross-sectional view illustrating an example in which an inner plug of a first embodiment is mounted in an opening part of a container body.

FIG. 1 illustrates an example in which an inner plug 10 of a first embodiment is mounted in an opening part 2 of a container body 1. An eye drop container of the first embodiment is constituted of a dripping container including the inner plug 10 that has a nozzle part 11, and the container body 1 that has the opening part 2 in which the inner plug 10 is mounted. The container body 1 has a storage part 5 for storing a content in a direction opposite to a direction in which the nozzle part 11 protrudes from the opening part 2. The container body 1 of this embodiment has a bottomed cylindrical shape, the opening part 2 has a cylindrical shape having a smaller outer diameter than the container body 1, the nozzle part 11 also has a cylindrical shape, and all of these are coaxially disposed. A content is a content constituted of a liquid or a content including a liquid. When the inner plug 10 is mounted in the opening part 2, the nozzle part 11 of the inner plug 10 constitutes a nozzle of the container body 1. In FIG. 1, in a general stationary state, the nozzle part 11 is disposed above, and the storage part 5 is disposed below. When the eye drop container is used, the nozzle part 11 is disposed downward or obliquely downward. In addition, when the eye drop container is stored, the nozzle part 11 may be placed sideways.

The nozzle part 11 has a nozzle hole 12 leading to the storage part 5. A content stored in the storage part 5 is dripped to the outside of the container body 1 through the nozzle hole 12. The inner plug 10 of the first embodiment has a disk-shaped flange part 13 which comes into contact with an annular tip surface 2a of the opening part 2, a cylindrical leg part 14 which has a narrowed lower end coming into contact with an inner surface 2b of the opening part 2, and a cylindrical inner cylinder part 16 which has a shape in which the nozzle part 11 extends toward the storage part 5 on an inner side of the leg part 14. An outer diameter of the flange part 13 in this example almost coincides with an outer diameter of the opening part 2. The nozzle hole 12 is formed to have a continuously linear shape to a tip 16a of the inner cylinder part 16. An annular clearance part 17 is formed between an inner surface of the leg part 14 and an outer surface of the inner cylinder part 16. In this example, a lower end of the inner cylinder part 16 is positioned above the lower end of the leg part 14. An upper part of the leg part 14 has a cylindrical shape, and a lower part thereof has a tapered shape narrowing downward in a conical shape. All of the foregoing cylindrical constituent elements can also have a polygonal tubular shape as necessary.

Figure 2:
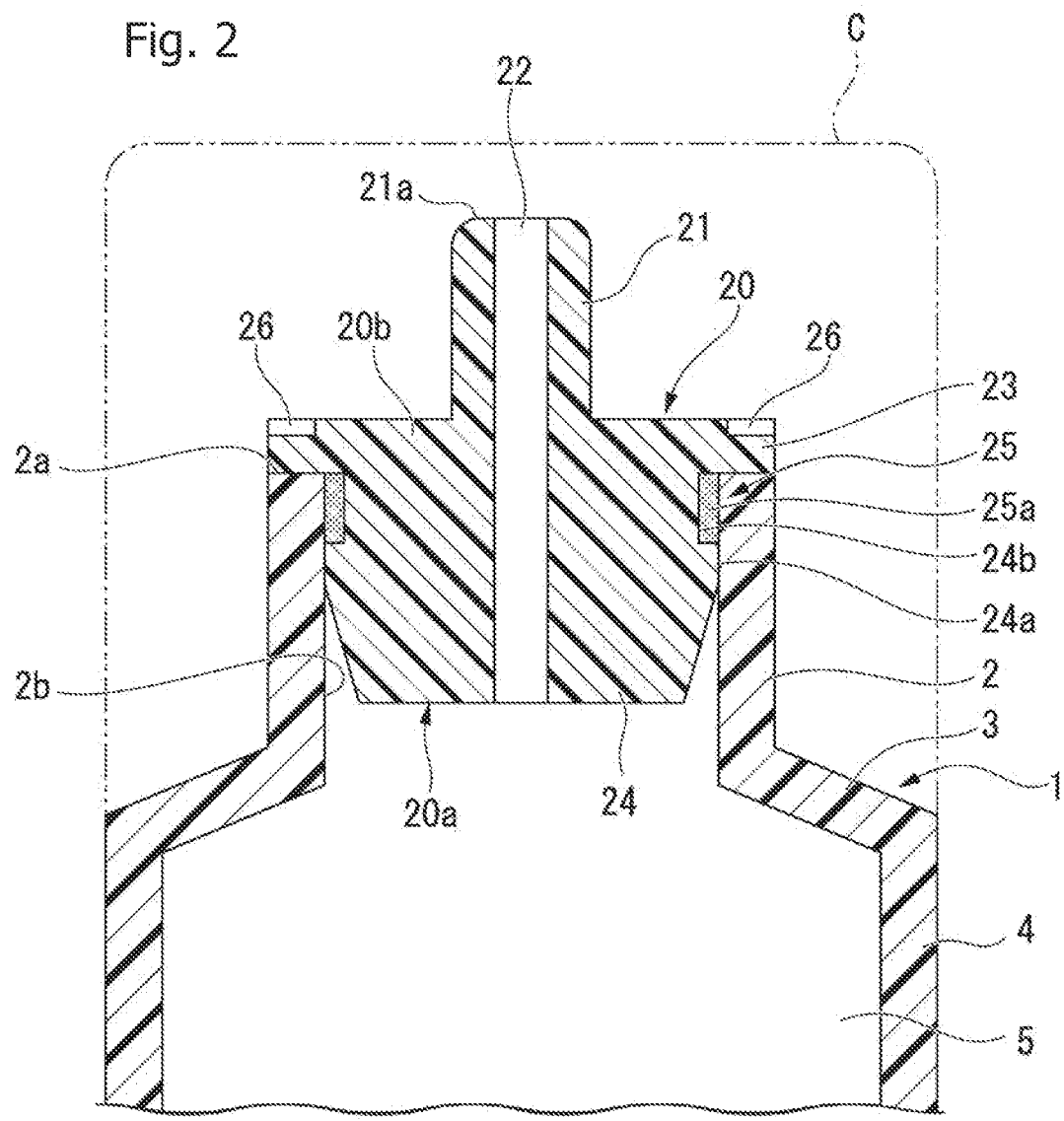
FIG. 2 is a cross-sectional view illustrating an example in which an inner plug of a second embodiment is mounted in an opening part of a container body.

FIG. 2 illustrates an example in which an inner plug 20 of a second embodiment is mounted in the opening part 2 of the container body 1. In the inner plug 20 of the second embodiment, an inner side of a leg part 24 is filled with a resin up to an inner surface of a nozzle hole 22, and the inner plug 20 does not have the inner cylinder part 16 and the clearance part 17 of the first embodiment. Other than those above, the inner plug 20 is constituted in a manner similar to that of the inner plug 10 of the first embodiment. In this case, even if the leg part 24 has a thick wall, occurrence of defective molding can be suppressed by molding the leg part 24 with a resin including a cyclic olefin copolymer. A nozzle part 21, a flange part 23, and the like can be constituted in a manner similar to those of the first embodiment.

The inner plug 10 or 20 has a liquid-contacting part 10a or 20a which is constituted of a layer including a cyclic olefin copolymer, and cushioning part 15 or 25 which is provided in an outer circumferential part in contact with the opening part 2. The liquid-contacting part 10a or 20a of the inner plug 10 or 20 is at least a part or the entirety of parts which may come into contact with a liquid (content). Examples of a part which may constitute the liquid-contacting part 10a or 20a include an inner surface of the nozzle part 11 or 21 of the nozzle hole 12 or 22, an inner surface of the flange part 13 or 23, an inner surface and an outer surface of the leg part 14 or 24, and an inner surface and an outer surface of the inner cylinder part 16. Here, the inner surfaces of the nozzle part 11 or 21, the leg part 14 or 24, and the inner cylinder part 16 are surfaces on an inner side in a radial direction centering on the nozzle hole 12 or 22. In addition, the inner surface of the flange part 13 or 23 is a surface on a side opposite to a side where the nozzle part 11 or 21 protrudes toward a tip 11a or 21a. The outer surfaces thereof are surfaces on a side opposite to the respective inner surfaces. In the inner plug 10 or 20, the entire part other than the cushioning part 15 or 25 may be constituted of a resin including a cyclic olefin copolymer as an inner plug main body 10b or 20b.

The inner plug 10 or 20 has a layer including a cyclic olefin copolymer as a resin having excellent non-sorption properties (non-adsorption properties). Examples of a cyclic olefin copolymer generally include so-called copolymers of cyclic olefins different from each other (COP), and copolymers of a cyclic olefin and an acyclic olefin (COC). Accordingly, sorption of a content with respect to the inner plug 10 or 20 can be suppressed.

Examples of a copolymer of cyclic olefins different from each other (COP) include a copolymer of cyclic olefins of two or more kinds, and hydrogenated products thereof. A copolymer of cyclic olefins different from each other (COP) is preferably an amorphous polymer and is more preferably a ring-opened polymer of cyclic olefins from metathesis or the like, or hydrogenated products thereof. A copolymer of cyclic olefins different from each other (COP) has a higher content proportion of alicyclic structures than a copolymer of a cyclic olefin and an acyclic olefin (COC) or the like and has excellent non-sorption properties (non-adsorption properties).

Examples of a copolymer of a cyclic olefin and an acyclic olefin (COC) include a copolymer of at least one kind of a cyclic olefin and at least one kind of an acyclic olefin, and hydrogenated products thereof. A copolymer of a cyclic olefin and an acyclic olefin (COC) is preferably an amorphous polymer and is more preferably a copolymer of a cyclic olefin and ethylene, or hydrogenated products thereof.

A cyclic olefin used as a constituent monomer of a cyclic olefin copolymer is an unsaturated hydrocarbon (olefin) having at least one ring structure. Examples thereof include at least one kind of vinyl cycloalkane having cycloalkane with a number of carbon atoms of 3 to 20 and derivatives thereof, monocycloalkene with a number of carbon atoms of 3 to 20 and derivatives thereof, and a cyclic olefin having a norbornene skeleton (norbornene-based monomer).

Examples of a norbornene-based monomer include bicyclo[2.2.1]-2-heptene (norbornene) and derivatives thereof. Examples of a norbornene derivative include a compound which has a substituent group such as an alkyl group, a compound which has two or more unsaturated bonds as norbornadiene, and a compound which has three or more ring structures and in which two ring structures thereof constitute a norbornene skeleton. Examples of a norbornene-based monomer having three or more ring structures include tricyclo[5.2.1.02,6]decene (dihydrodicyclopentadiene), a compound in which one or more molecules of cyclopentadiene are added to norbornene or dihydrodicyclopentadiene by Diels-Alder reaction (for example, tetracyclododecene, pentacyclopentadecene, or hexacycloheptadecene), hydrogenated products thereof, isomers in which positions of double bonds differ, and an alkyl substituent.

Examples of an acyclic olefin used as a constituent monomer of a copolymer of a cyclic olefin and an acyclic olefin (COC) include α-olefins such as ethylene, propylene, 1-butene, 1-pentene, 1-hexene, 1-heptene, and 1-octene; and alkenes such as 3-decene and 3-dodecene.

Resin components constituting the liquid-contacting part 10a or 20a or the inner plug main body 10b or 20b may be at least only one kind of a cyclic olefin copolymer or may be a mixture of a cyclic olefin copolymer and other resins or the like. Examples of a proportion of the cyclic olefin copolymer in the liquid-contacting part 10a or 20a or the inner plug main body 10b or 20b include 40 to 100 weight %. Examples of other resins which may be mixed into the liquid-contacting part 10a or 20a or the inner plug main body 10b or 20b include a polyolefin resin such as a polyethylene resin, and a thermoplastic elastomer such as a styrene-based elastomer or an olefin-based elastomer.

In the liquid-contacting part 10a or 20a, a thickness of the layer including a cyclic olefin copolymer (sorption curbing layer) is not particularly limited. However, it is preferable to be within a range of 50 to 3,000 μm. Specific examples of the thickness of the sorption curbing layer include 50 μm, 100 μm, 150 μm, 200 μm, 300 μm, 350 μm, 400 μm, 450 μm, 500 μm, 1,000 μm, 1,500 μm, 2,000 μm, 2,500 μm, 3,000 μm, and a range including thicknesses therebetween. A part thicker than the foregoing range may be present in the sorption curbing layer. For example, as in the inner plug main body 10b or 20b, when a sorption curbing layer is provided all the way to the inner side of the inner plug 10 or 20 beyond the liquid-contacting part 10a or 20a, a part thicker than 3,000 μm may be present therein. The proportion of the sorption curbing layer to the surface of the liquid-contacting part 10a or 20a is preferably 80% or higher in terms of surface area ratio, and examples thereof include approximately 90%, approximately 95%, and approximately 100%.

The cushioning part 15 or 25 is provided on at least an outer circumferential surface of the leg part 14 or 24. The outer circumferential surface of this leg part 14 or 24 is an example of an outer circumferential part in contact with the opening part 2 of the inner plug 10 or 20.

In the first embodiment in FIG. 1, in the cushioning part 15, a cylindrical part 15a formed on an upper outer circumferential surface of the leg part 14 and an annular plate-shaped part 15b formed on a lower surface of the flange part 13 are continuously formed, and a cross section thereof has an L-shape.

In the second embodiment in FIG. 2, the cushioning part 25 has a cylindrical part 25a formed on an upper outer circumferential surface of the leg part 24, but nothing is formed on a lower surface of the flange part 23. The flange part 23 directly comes into contact with the tip surface 2a of the opening part 2. Since the cushioning part 15 or 25 is provided in at least a part of the outer circumferential part in contact with the opening part 2 of the inner plug 10 or 20, the cushioning part 15 or 25 constituted of a softer material than the liquid-contacting part 10a or 20a or the inner plug main body 10b or 20b is in contact with the opening part 2. Therefore, occurrence of a gap between the inner plug 10 or 20 and the container body 1 can be suppressed. The cushioning part 15 or 25 may be provided in the entire outer circumferential part in contact with the opening part 2 of the inner plug 10 or 20.

The part 15b in which the cushioning part 15 is formed in the flange part 13 is formed on a side where at least the flange part 13 faces the tip surface 2a of the opening part 2, that is, on the lower surface in this example. A range of the part 15b in which the cushioning part 15 is formed in the flange part 13 is not particularly limited. The cushioning part 15 may be extended to the outer circumferential surface of the flange part 13 in the radial direction. Moreover, the cushioning part 15 can also be extended to a side where the nozzle part 11 protrudes from the flange part 13, that is, to an upper surface side in this example.

The cushioning part 15 or 25 is preferably formed to have a continuous ring shape in a circumferential direction centering on the nozzle hole 12 or 22, but the cushioning part 15 or 25 can also be formed in only a part of the inner plug 10 or 20 in the circumferential direction. For example, a plurality of cushioning parts 15 or 25 may be formed in the circumferential direction at predetermined intervals. Preferably, they may be intermittently formed with regular intervals therebetween. Alternatively, one or a plurality of parts where the cushioning part 15 or 25 is not provided may be locally disposed in parts in the circumferential direction, and the cushioning parts 15 or 25 may be provided in parts other than those in a C-shape in the circumferential direction.

For example, the cushioning part 15 or 25 can be constituted using a material such as a resin selected from a polyethylene resin, a rubber, an elastomer, and the like. The thickness of the cushioning part 15 or 25 is not particularly limited, and examples thereof include 50 μm, 100 μm, 150 μm, 200 μm, 300 μm, 350 μm, 400 μm, 450 μm, 500 μm, 1,000 μm, and a range including thicknesses therebetween. As long as a liquid (content) does not come into contact with the cushioning part 15 or 25, the thickness of the cushioning part 15 or 25 may be larger than the foregoing numerical values.

Examples of a polyethylene resin constituting the cushioning part 15 or 25 include a homopolymer of ethylene (ethylene homopolymer), linear low-density polyethylene in which ethylene and an α-olefin (1-butene or the like) with a number of carbon atoms of 4 are copolymerized (C4-LLDPE), linear low-density polyethylene in which ethylene and α-an olefin (1-hexene or the like) with a number of carbon atoms of 6 are copolymerized (C6-LLDPE), linear low-density polyethylene in which ethylene and an α-olefin (1-octene or the like) with a number of carbon atoms of 8 are copolymerized (C8-LLDPE), an ethylene-vinyl acetate copolymer (EVA), and an ethylene-vinyl alcohol copolymer (EVOH).

Examples of a rubber or an elastomer constituting the cushioning part 15 or 25 include a natural rubber, a synthetic rubber, and a thermoplastic elastomer such as a styrene-based elastomer or an olefin-based elastomer. Resin components constituting the cushioning part 15 or 25 may be at least only one kind of a polyethylene resin, a rubber, and an elastomer; may be a mixture of two or more kinds of a polyethylene resin, a rubber, and an elastomer; or may be a mixture with other resins or the like. Examples of a proportion of a polyethylene resin, a rubber, or an elastomer in the cushioning part 15 or 25 include 50 to 100 weight %. Examples of other resins which may be mixed into the cushioning part 15 or 25 include a polyolefin resin such as a polypropylene resin.

Another layer may be provided between the liquid-contacting part 10a or 20a or the inner plug main body 10b or 20b and the cushioning part 15 or 25. When adhesive properties between resin layers are not hindered, the liquid-contacting part 10a or 20a or the inner plug main body 10b or 20b and the cushioning part 15 or 25 may be laminated such that they come into direct contact with each other. When another layer is interposed between the liquid-contacting part 10a or 20a or the inner plug main body 10b or 20b and the cushioning part 15 or 25, the thickness of another layer is preferably 150 μm or shorter, for example.

The outer circumferential surface of the leg part 14 or 24 may have a cylindrical part 14a or 24a in which the liquid-contacting part 10a or 20a or the inner plug main body 10*b* or 20*b* comes into direct contact with the inner surface 2*b* of the opening part 2 on a side closer to the storage part 5 of the container body 1 than a part 14*b* or 24*b* in contact with the inner surface 2*b* of the opening part 2 via the cushioning part 15 or 25. Since the liquid-contacting part 10*a* or 20*a* or the inner plug main body 10*b* or 20*b* comes into direct contact with the inner surface 2*b* of the opening part 2 in this part 14*a* or 24*a*, contact between a content and the cushioning part 15 or 25 can be suppressed.

In the outer circumferential part in contact with the opening part 2 of the inner plug 10 or 20, regarding a proportion between a surface area (A) of the part 14*a* or 24*a* in which the liquid-contacting part 10*a* or 20*a* or the inner plug main body 10*b* or 20*b* is in contact with the inner surface 2*b* of the opening part 2 and a surface area (B) of a part in which the inner plug 10 or 20 is in contact with the inner surface 2*b* of the opening part 2 via the cushioning part 15 or 25, in order to enhance an effect of buffering by the cushioning part 15 or 25, it is preferable that the ratio of (A)/(B) be small. Examples of (A)/(B) include 0.3 or smaller, 0.2 or smaller, 0.1 or smaller, approximately 0.05, approximately 0.02, and approximately 0.01. The cushioning part 15 or 25 may extend to a part in the vicinity of a boundary part between the outer circumferential part in contact with the opening part 2 of the inner plug 10 or 20 and the liquid-contacting part 10*a* or 20*a*. When the cushioning part 15 or 25 is in contact with a part in which a gap is generated between the inner plug 10 or 20 and the inner surface of the opening part 2, it is preferable that a width of the cushioning part 15 or 25 in contact with the foregoing gap be short.

Regarding production of the inner plug 10 or 20, the cushioning part 15 or 25 may be joined by heat seal, adhesion, or the like after the inner plug main body 10*b* or 20*b* is molded, the inner plug main body 10*b* or 20*b* and the cushioning part 15 or 25 may be resin-molded at the same time using two-color molding or the like. In addition, after the inner plug main body 10*b* or 20*b* is molded, the cushioning part 15 or 25 may be resin-molded between the inner plug main body 10*b* or 20*b* and a mold by insert molding. In a case of insert molding, it is preferable that the shape of the inner plug main body 10*b* or 20*b* be maintained during molding of the cushioning part 15 or 25. For this reason, it is preferable that a melting point (or a heat resistance or the like) of a material constituting the inner plug main body 10*b* or 20*b* be higher than the molding temperature of the cushioning part 15 or 25. When the inner plug main body 10*b* or 20*b* is molded using a mold, for example, as illustrated in FIG. 2, a gate part 26 for injecting a resin into the mold may be disposed in the vicinity of an end part of the flange part 23, for example. If the gate part 26 is disposed in at least two or more parts in the circumferential direction of the flange part 23, a flow of a resin can be made smoother.

The container body 1 has the opening part 2 in which the inner plug 10 or 20 is mounted, and a body part 4 which surrounds the storage part 5. A shoulder part 3 which decreases in diameter in stages may be provided between the opening part 2 and the body part 4. It is preferable that at least the container body 1 have a layer including a cyclic olefin copolymer on at least a surface in contact with a liquid content. A resin including a cyclic olefin copolymer used in the container body 1 may be suitably designed from alternatives similar to the resin including a cyclic olefin copolymer used in the liquid-contacting part 10*a* or 20*a* or the inner plug main body 10*b* or 20*b* of the inner plug 10 or 20 described above. However, these resins may be the same or may be different resins.

The container body 1 may have a reinforcement layer, a gas barrier layer, a UV absorption layer, an oxygen absorption layer, a print layer, or the like. Examples of a method for laminating layers constituting the container body 1 include dry lamination, extrusion lamination, coextrusion, and coating, and the method can be suitably selected in accordance with the material, the combination, or the like of layers. The entire container body 1 may be colorless and transparent, and a part or the entirety thereof in a thickness direction or a surface direction may be colored. A method for molding the container body 1 is not particularly limited, and examples thereof include blow molding. A kind of the container of the container body 1 is not particularly limited, and examples thereof include a bottle container.

The eye drop container may have a cap C in order to protect the nozzle part 11 or 21. It is preferable that the cap C be coupled to at least any of the nozzle part 11 or 21 of the inner plug 10 or 20, and the opening part 2, the shoulder part 3, and the body part 4 of the container body 1 in an opening/closing manner or an attachable/detachable manner. A capacity of the storage part 5 is not particularly limited. However, it is 20 ml or smaller, and examples thereof include 3 ml, 5 ml, 10 ml, 15 ml, and 20 ml.

Examples of eye drops include aqueous eye drops, oil-based eye drops, use-time soluble eye drops, and suspension eye drops. Eye drops may contain a solubilizer, a stabilizer, an isotonic agent, a buffer agent, a pH regulator, a preservative, a thickening agent, or the like as an additive agent other than active components.

Specific examples of active components used in eye drops include isopropyl unoprostone, latanoprost, travoprost, tafluprost, and bimatoprost as prostaglandin-related drugs; diclofenac sodium, pranoprofen, bromphenac sodium hydrate, and nepafenac as non-steroidal anti-inflammatory drugs; cyanocobalamin and flavin adenine dinucleotide sodium as vitamin B preparations; acitazanolast hydrate, amlexanox, ibudilast, epinastine hydrochloride, olopatadine hydrochloride, sodium cromoglycate, ketotifen fumarate, tranilast, pemirolast potassium, and levocabastine hydrochloride as anti-allergic components; cyclosporine and tacrolimus hydrate as immunosuppressive drugs; carteolol hydrochloride, timolol maleate, niprazirol, betaxolol hydrochloride, and levobnorol hydrochloride as β-blockers, bunazosin hydrochloride as an al-blocker; brimonidine tartrate as an α2-stimulant; pilocarpine hydrochloride as a parasympathomimetic agent; dipivefrine hydrochloride as a sympathomimetic drug; distigmine bromide as a cholinesterase inhibitor; glutathione and pyrenoxin as cataract remedies; gatifloxacin hydrate, dibekacin sulfate, tosufloxacin tosylate hydrate, tobramycin, vancomycin hydrochloride, moxifloxacin hydrochloride, levofloxacin hydrate, lomefloxacin hydrochloride, ofloxacin, chloramphenicol, and norfloxacin as antibacterial drugs; and dorzolamide hydrochloride and brinzolamide as β-blockers/carbonic anhydrase inhibitor compounding agents.

Hereinabove, description has been given on the basis of the preferred embodiments of the present invention. However, the present invention is not limited to the embodiments described above, and various modifications and changes can be made within a range not departing from the gist of the present invention.

A dripping container having the inner plug of the present embodiment is not limited to an eye drop container and can also be applied to a container for storing other contents.

Examples thereof include containers for nasal drops, eardrops, and a chemical agent, a lotion, and the like of a type of dripping a drug solution on a lesion at the time of administration.

Regarding a layer including a cyclic olefin copolymer, in place of a cyclic olefin copolymer or together with a cyclic olefin copolymer, a homopolymer of a cyclic olefin or hydrogenated products thereof can be mixed thereinto.

EXAMPLES

Hereinafter, the present invention will be specifically described using Examples.
(Manufacturing of Inner Plug)
An inner plug having an annular cushioning part on an outer circumferential surface was manufactured while a COP was adopted as a material of an inner plug main body and PE was adopted as a material of a cushioning part. In Example 1, an inner cylinder part was provided on an inner side of a leg part of the inner plug main body via a clearance. In Example 2, a structure in which an inner side of a leg part of the inner plug main body was filled with a resin up to a nozzle hole was adopted. For the sake of comparison, in Comparative Example 1, the cushioning part was omitted, and the inner plug was manufactured using PE.
(Measurement of Residual Rate)
In each of brown glass bottles having a diameter of 24 mm and a height of 45 mm, one inner plug and 3 ml of a lotion "REVITAL (registered trademark) lotion EX I" (liquid content) of Shiseido Co., Ltd. were input, and the brown glass bottles were sealed with an aluminum tape. The entire inner plugs were immersed into the liquid contents, mouths of the brown glass bottles were sealed using an aluminum tape in lids, and the lotions were stored under an environment of a temperature of 40° C. and a relative humidity of 75%. The concentrations of tocopherol acetate (vitamin E) in the liquid contents before immersion of the inner plugs (initial concentrations) were approximately 477 ppm. The concentrations of the tocopherol acetate (vitamin E) in the liquid contents after being stored for 28 days (concentrations after immersion) were measured. Based on the initial concentrations and the concentrations after immersion, a residual rate is calculated as in the following Expression 1.

Residual rate (%)=(concentrations after immersion/ initial concentrations)×100(%)   (Expression 1)

In Example 1, the concentrations after immersion were approximately 427 ppm, and the residual rate was approximately 89.5%.
In Example 2, the concentrations after immersion were approximately 428 ppm, and the residual rate was approximately 89.7%.
In Comparative Example 1, the concentrations after immersion were approximately 341 ppm, and the residual rate was approximately 71.5%.
(Leakage Test)
Container main bodies in which the capacity of a storage part was 6.9 ml and an innermost layer was constituted of a cyclic olefin resin were prepared. The inner plugs of Examples 1 and 2 and Comparative Examples 1 and 2 were respectively mounted in opening parts of the container main bodies. The inner plugs of Examples 1 and 2 and Comparative Example 1 were the same as those used in measurement of the residual rate. In addition, the entire inner plug of Comparative Example 2 was manufactured using a cyclic olefin resin.

Examples 1 and 2 were constituted such that the cushioning part of the inner plug comes into contact with the innermost layer of the cyclic olefin resin in the opening part of the container body.
A bottom part was cut out from the storage part of the container body, and an opening part for injecting an inspection liquid which will be described was formed. In addition, a nozzle part of the inner plug mounted in the opening part of the container body was sealed with an aluminum film. The container body was placed in an opposite direction such that the nozzle part faces downward and the bottom part of the container body faces upward, and an inspection liquid (manufactured by Ichinen Chemicals Co., Ltd., Heat Seal Checker JIP310, with a red dye therein) was injected through the opening part. After the container body was kept in a standstill state in the opposite direction for a week, a contact part between the opening part of the container body and the inner plug was wiped using white cloth or the like (wiping tool), and it was judged whether or not there is leakage of the content by recognizing the red inspection liquid on the white wiping tool.
In Examples 1 and 2 and Comparative Example 1, there was no leakage in the contact part between the opening part of the container body and the inner plug.
In Comparative Example 2, leakage was confirmed in the contact part between the opening part of the container body and the inner plug.
(Conclusion)
In Examples 1 and 2 in which the cushioning part was provided in the outer circumferential part in contact with the opening part of the container body, the residual rate of the components was high, and there was no leakage in the contact part between the opening part and the inner plug.
In Comparative Example 1 in which the entire inner plug was constituted of PE, there was no leakage in the contact part between the opening part and the inner plug, but the residual rate of the components was low.
In Comparative Example 2 in which the entire inner plug was constituted of a cyclic olefin resin, it was presumed that the residual rate of the components was high in a manner similar to those of Examples 1 and 2, but leakage of the content occurred in the contact part between the opening part and the inner plug.
From the foregoing results, according to the inner plugs of Examples 1 and 2, it was confirmed that a gap or leakage was unlikely to occur between the inner plug and the container body while sorption (adsorption, absorption) of eye drops with respect to the inner plug was suppressed.

INDUSTRIAL APPLICABILITY

An inner plug according to an aspect of the present invention has a liquid-contacting part that is constituted of a layer including a cyclic olefin copolymer having excellent non-sorption properties, and a cushioning part that is provided in an outer circumferential part in contact with an opening part. Therefore, generation of a gap between a container body and the inner plug can be suppressed while sorption (adsorption, absorption) of eye drops is suppressed. Therefore, the present invention can be industrially utilized.

REFERENCE SIGNS LIST

C Cap
1 Container body
2 Opening part
2a Tip surface of opening part

2b Inner surface of opening part
3 Shoulder part
4 Body part
5 Storage part
10, 20 Inner plug
10a, 20a Liquid-contacting part
10b, 20b Inner plug main body
11, 21 Nozzle part
11a, 21a Tip of nozzle part
12, 22 Nozzle hole
13, 23 Flange part
14, 24 Leg part
14a, 24a Part in which leg part directly comes into contact with opening part
14b, 24b Part in contact with inner surface of opening part via cushioning part
15, 25 Cushioning part
15a, 25a Part in which cushioning part is formed in leg part
15b Part in which cushioning part is formed in flange part
16 Inner cylinder part
16a Tip of inner cylinder part
17 Clearance
26 Gate part

What is claimed is:

1. An inner plug to be mounted in an opening part of a container body and constituting a nozzle, the inner plug comprising:
    a liquid-contacting part having a surface comprising a layer including a cyclic olefin copolymer; and
    a cushioning part that is provided in an outer circumferential part in contact with the opening part,
    wherein the liquid-contacting part has a leg part which has a cylindrical shape and comes into contact with a cylindrical inner surface of the opening part,
    the cushioning part has a cylindrical part provided in an outer circumferential surface of the leg part in contact with the cylindrical inner surface of the opening part,
    wherein the liquid-contacting part is configured such that the surface comes into contact with a content of the container body when the inner plug is mounted in the opening part of the container body,
    the cushioning part is configured not to contact with the content by being separated by the liquid-contacting part when the inner plug is mounted in the opening part of the container body, and
    the cushioning part is constituted of a material of one or more kinds selected from a polyethylene resin, a rubber, and an elastomer.

2. The inner plug according to claim 1,
    wherein the inner plug has a flange part which comes into contact with a tip surface of the opening part.

3. The inner plug according to claim 2, wherein the cylindrical part of the cushioning part is formed on an upper outer circumferential surface of the leg part and an annular plate-shaped part is formed on a lower surface of the flange part, and the cylindrical part and the annular plate-shaped part are continuously formed to have an L-shaped cross section.

4. The inner plug according to claim 2, wherein the cylindrical part of the cushioning part is formed on an upper outer circumferential surface of the leg part and the cushioning part does not have a part formed on a lower surface of the flange part.

5. The inner plug according to claim 1,
    wherein the outer circumferential part of the inner plug in contact with the opening part of the container body has a part in which the liquid-contacting part directly comes into contact with the inner surface of the opening part on a side closer to a storage part of the container body than a part in contact with the inner surface of the opening part via the cushioning part.

6. The inner plug according to claim 1,
    wherein the layer including the cyclic olefin copolymer includes at least one of a COP that is a copolymer of cyclic olefins different from each other and a COC that is a copolymer of a cyclic olefin and an acyclic olefin.

7. An eye drop container comprising:
    the inner plug according to claim 1; and
    a container body that has an opening part in which the inner plug is mounted.

8. The eye drop container according to claim 7,
    wherein the container body has a layer including a cyclic olefin copolymer on at least a surface in contact with a liquid content.

9. The inner plug according to claim 1, wherein the liquid-contacting part consists of a COP that is a copolymer of cyclic olefins different from each other.

10. The inner plug according to claim 1, wherein the cushioning part consists of a polyethylene resin, an elastomer, or a combination thereof.

11. The inner plug according to claim 1, wherein a thickness of the cushioning part is between 50 μm and 1000 μm.

* * * * *